United States Patent [19]

Murthy et al.

[11] Patent Number: 6,107,490

[45] Date of Patent: Aug. 22, 2000

[54] PROCESS FOR THE MANUFACTURE OF 4-METHYL-5-HYDROXYMETHYL-IMIDAZOLE

[75] Inventors: K. S. Keshava Murthy; Gamini Weeratunga; Derek John Norris, all of Brantford, Canada

[73] Assignee: Brantford Chemicals Inc., Brantford, Canada

[21] Appl. No.: 08/571,779

[22] Filed: Dec. 13, 1995

[51] Int. Cl.[7] .................................................. C07D 233/64
[52] U.S. Cl. .......................................................... 548/341.1
[58] Field of Search ........................................... 548/341.1

[56] References Cited

U.S. PATENT DOCUMENTS

| 4,189,591 | 2/1980 | Mueller et al. | 548/342 |
| 4,275,216 | 6/1981 | Hubert-Brierre | 542/342 |

*Primary Examiner*—Patricia L. Morris
*Attorney, Agent, or Firm*—Ivor M. Hughes; Neil H. Hughes; Marcelo K. Sarkis

[57] ABSTRACT

A process is provided for the manufacture of 4-lower-alkyl-5-hydroxymethyl-imidazole comprising reacting (4)-lower-alkyl imidazole with formaldehyde in an alkanol solvent having from 2 to 5 carbon atoms in the presence of a solid mild base suspended in the solvent.

9 Claims, No Drawings

PROCESS FOR THE MANUFACTURE OF 4-METHYL-5-HYDROXYMETHYL-IMIDAZOLE

FIELD OF THE INVENTION

This invention relates to the manufacture of 4-methyl-5-hydroxymethylimidazole.

BACKGROUND OF THE INVENTION

As indicated in U.S. Pat. No. 4,189,591, 4-methyl-5-hydroxymethylimidazole was discovered by WINDAUS in 1909 and was made by the reaction of formaldehyde with 4-methylimidazole. This product is a suitable intermediate for making Cimetidine.

U.S. Pat. No. 4,189,591 was purportedly directed to making this product by an improved process. The improved process was purportedly carried out in aqueous reaction media. The Patent specifies the reaction must be carried out under closely controlled conditions (column 1, lines 31–32). The patent also specifies that when the water is replaced by methanol, only trace amounts of 4-methyl-5-hydroxymethyl-imidazole was found in the reaction mixture (column 2, line 67–column 3, line 1). According to the patent, "the other common solvents are no better . . ." (column 3, lines 1–2).

With each of the processes, there are deficiencies relating to reactants, conditions of reactions and yields.

In U.S. Pat. No. 4,275,216, a process is provided by which 4(5)-hydroxymethyl- 5(4)-lower- alkyl imidazoles may be manufactured. The process reacts 5(4)-lower alkyl imidazole with formaldehyde in the presence of a strong base (for example, a mineral base such as sodium hydroxide, tertiary amine, quarternary ammonium hydroxide and alkaline metal alcoholates) and at a reaction temperature of 60–95° C.

It is therefore an object of this invention to provide an improved process which is easier to use and more environmentally friendly providing the ability to separate easily and recover non-reactant materials (such as the solvent and mild base) used in the process.

Further and other objects of the invention will be realized by those skilled in the art from the following Summary of Invention and Detailed Description of Embodiments Thereof.

SUMMARY OF INVENTION

Unexpectedly, we have found that by carrying out the reaction of the 4-methylimidazole with formaldehyde in an alkanol (other than methanol) and preferably isopropanol, good yields are achieved in the manufacture of 4-methyl-5-hydroxymethylimidazole. Preferably anhydrous potassium carbonate ($K_2CO_3$) or other such mild base is added in solid form and suspended in the reaction mixture to catalyze the reaction.

After the reaction is completed the suspended potassium carbonate when used is removed by filtration.

Therefore according to one aspect of the invention, a process for the manufacture of 4-lower-alkyl-5-hydroxymethylimidazoles such as 4-methyl-5-hydroxymethylimidazole is provided comprising reactive formaldehyde (whose source may be paraformaldehyde which when heated degrades into formaldehyde) with 4-methyl-imidazole in an alkanol solvent (other than methanol) (for example having 2–5 carbon atoms) for example isopropanol in the presence of a solid mild base (for example, a base of a weak acid such as potassium carbonate) suspended in the solvent.

DETAILED DESCRIPTION OF PREFERRED EMBODIMENTS OF THE INVENTION

EXAMPLE 1

Preparation of 4-methyl-5-hydroxymethylimidazole hydrochloride

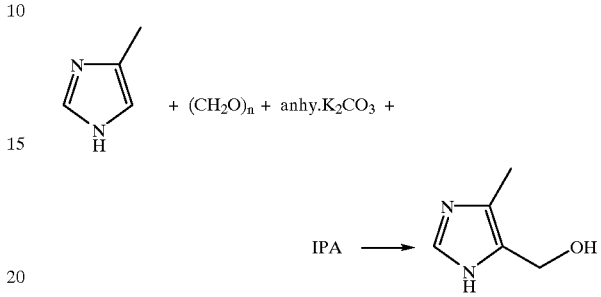

A mixture containing 4-methylimidazole (30 g, 365 mmol), paraformaldehyde (12 g, 402 mmol), potassium carbonate (55 g, 402 mmol) and industrial isopropanol (150 mL) is heated to 50° C. for 20 h. The reaction mixture is cooled to room temperature and filtered. Hydrogen chloride gas is bubbled through the filtrate at 25° C. until the solution becomes acidic. Acetone (200 mL) was added and cooled to 15° C. for ½ h. The precipitate was filtered, washed with Acetone/IPA (1:1) mixture (30 mL) and dried to give 32.4 g of the hydrochloride salt of the aimed product (60%).

EXAMPLE 2

A mixture containing 4-methylimidazole (100 g), paraformaldehyde (40 g), potassium carbonate (193 g) and isoproponal (500 ml) is heated to 50° C. for 20h. The reaction mixture is cooled to room temperature and filtered to remove the potassium carbonate. Concentrated HCl (35% HCl in water) (230 ml) is added to the filtrate (solution) with cooling (below room termperature—for example, less than 20° C.). The solution was stirred at room temperature for 1 hour and the solvent removed to give 258 g of the crude product.

The recovered product is recrystallized from n-butanol acetone mixture (2:4) to yield the hydrochloride salt of the pure product (50% yield after purification).

EXAMPLE 3

A mixture containing 4-methylimidazole (10 g, 122 mmol), paraformaldehyde (4 g, 134 mmol), potassium carbonate (1.7 g, 12.2 mmol) (catalytic amount of mild base) and isopropanol (20 mL) is heated to 50–55° for 20 hours. The reaction mixture is cooled to room temperature and filtered. Concentrated Hydrochloric acid is added to the filtrate with cooling until the solution becomes acidic. The mixture was stirred at room temperature for 1 hour and the solvent was removed under reduced pressure. The product was crystallized from an acetone: MeOH (6:1) mixture (70 mL) to give 8.9 g of the expected product (49%).

As many changes may be made to the emodiments without departing from the scope of the invention, it is intended that all material contained herein be interpreted as illustrative of the invention and not in a limiting sense.

The embodiments of the invention in which an exclusive property or privilege is claimed are as follows:

1. A process for the manufacture of 4-lower-alkyl-5-hydroxymethylimidazole comprising reacting (4)-lower-alkyl imidazole with formaldehyde in an alkanol solvent having from 2 to 5 carbon atoms in the presence of a solid mild base suspended in the solvent.

2. The process of claim 1 wherein the alkanol is isopropanol.

3. The process of claims 1 or 2 wherein the solid mild base suspended in the solvent is potassium carbonate.

4. The process of claims 1 or 2 wherein the process further comprises recovering the 4-lower-alkyl-5-hydroxymethyl-imidazole.

5. The process of claim 3 wherein the process further comprises recovering the 4-lower-alkyl-5-hydroxymethyl-imidazole.

6. The process of claims 1 or 2 wherein the process for the production of the 4-lower-alkyl-5-hydroxymethyl-imidazole produces 4-methyl-5-hydroxymethylimidazole.

7. The process of claim 3 wherein the process for the production of the 4-lower-alkyl-5-hydroxymethyl-imidazole produces 4-methyl-5-hydroxymethylimidazole.

8. The process of claim 4 wherein the process for the production of the 4-lower-alkyl-5-hydroxymethyl-imidazole produces 4-methyl-5-hydroxymethylimidazole.

9. The process of claim 5 wherein the process of recovering the 4-lower-alkyl-5-hydroxymethyl-imidazole recovers 4-methyl-5-hydroxymethylimidazole.

* * * * *